_United States Patent_ [19]

De Felice

[11] 4,075,352

[45] * Feb. 21, 1978

[54] METHOD OF IMPROVING THE MYOCARDIAL FUNCTION BY THE ADMINISTRATION OF CARNITINE

[76] Inventor: Stephen L. De Felice, 430 Topping Hill Road, Westfield, N.J. 07090

[*] Notice: The portion of the term of this patent subsequent to Aug. 20, 1991, has been disclaimed.

[21] Appl. No.: 681,063

[22] Filed: Apr. 28, 1976

Related U.S. Application Data

[63] Continuation-in-part of Ser. No. 485,301, July 2, 1974, Pat. No. 3,968,241, which is a continuation-in-part of Ser. No. 303,772, Nov. 6, 1972, Pat. No. 3,830,931.

[51] Int. Cl.² ............................................. A61K 31/195
[52] U.S. Cl. .................................................... 424/319
[58] Field of Search ......................................... 424/319

[56] References Cited

U.S. PATENT DOCUMENTS

| 2,278,123 | 3/1942 | Heyn | 424/316 |
| 2,761,807 | 9/1956 | Borsook et al. | 424/316 |
| 3,830,931 | 8/1974 | De Filice | 424/319 |
| 3,968,241 | 7/1976 | De Filice | 424/319 |

_Primary Examiner_—Albert T. Meyers
_Assistant Examiner_—Daren M. Stephens
_Attorney, Agent, or Firm_—Jacobs & Jacobs

[57] ABSTRACT

The myocardial function of a human or animal heart to which the oxygen supply has been diminished is improved through parenteral administration of $\beta$-hydroxy-$\gamma$-trimethylaminobutyric acid or a pharmaceutically acceptable non-toxic salt thereof.

5 Claims, No Drawings

METHOD OF IMPROVING THE MYOCARDIAL FUNCTION BY THE ADMINISTRATION OF CARNITINE

This is a continuation-in-part of my copending application, Ser. No. 485,301, filed July 2, 1974, now U.S. Pat. No. 3,968,241 which application is a continuation-in-part of my application Ser. No. 303,772, filed Nov. 6, 1972, now U.S. Pat. No. 3,830,931.

Detailed Description

The present invention pertains to improving the myocardial function of a human or animal heart to which the oxygen supply has been diminished. Diminishment of the oxygen supply may occur, inter alia, during heart failure and during surgery involving the heart directly or indirectly.

It has now been discovered that the administration of β-hydroxy-γ-trimethylaminobutyric acid, or a pharmaceutically acceptable non-toxic salt thereof improves the myocardial function when the heart of a human or animal suffers a reduction of its oxygen supply. This substance is a well known compound, also known as carnitine, which has been safely used for a number of years for different indications. For example, the compound is sold in Europe as an appetite stimulant, and it has been reported that the material has an effect on the growth rate of children; see, e.g., Borniche et al., Clinic Chemica Acta, 5, 1960 and Alexander et al., "Protides in the Biological Fluids," 6th Colloquium, Bruges, 1958, pp 306-310. Investigation of the drug as an antagonist of thyroid hormone in cases of hyperthyroidism has also been reported, Gilgore et al., Journal of New Drugs, 6, No. 6, 319,320 (1966) and DeFelice et al., loc. cit., 6, No. 6, 351,353 (1966). Finally, the use of the drug in the treatment of angina pectoris has been described in my copending application, Ser. No. 157,741 filed June 28, 1971, now abandoned.

While the mechanism of action of β-hydroxy-γ-trimethylaminobutyric acid in these various conditions is not fully understood, there is no immediately apparent reason to expect from these previous uses that administration of carnitine or a pharmaceutically acceptable salt thereof would improve the myocardial function when the oxygen supply to the heart has been reduced or diminished.

β-hydroxy-γ-trimethylaminobutyric acid demonstrates a positive inotropic action on the myocardium, which contractile force is not associated with an abnormal decrease in heart rate. In addition to restoring the sinus rhythm to normal, β-hydroxy-γ-trimethylaminobutyric acid results in a significant increase in cardiac output. Dramatic diuresis with reversal of the hypotension and urine retention which can accompany congestive heart failure is often seen, together with a restoration of pulse and blood pressure. Significantly, the toxicity of β-hydroxy-γ-trimethylaminobutyric acid is remarkably low. The drug can thus be given orally or, more significantly parenterally, such as intravenously, without concern to toxic reactions. For improving the myocardial function, carnitine and its pharmaceutically acceptable salts is preferably administered parenterally.

Its properties can be seen in both animal models and clinical studies.

Thus in the isolated perfused Langendorf heart preparation, β-hydroxy-γ-trimethylaminobutyric acid effectively minimizes the reduction in the force of myocardial contraction during periods of reduced blood flow. This protection lasts for at least 60 minutes with no adverse effect on the vital functions of the heart itself. This may be seen from the following.

Twenty adult mongrel dogs weighing from 10–12 kg and of either sex were anesthetized with sodium pentobarbital, 30 mg/kg. A polyethylene catheter was placed in the right femoral artery to allow for the rapid removal of blood. Clotting was pevented by injecting 1000 units/kg heparin (sodium) into the femoral vein. The chest was opened by a midline incision and all major branches of the ascending aorta, except the brachiocephalic trunk, were ligated. The reservoir chamber of the perfusion system was filled with autologous blood drawn from the catheterized femoral artery of the same dog. The brachiocephalic artery was then cannulated with a short stainless steel cannula which was connected by polyethylene tubing to the pump perfusion circuit. At this time the descending aorta was ligated and the heart quickly removed from the chest cavity. The heart was then suspended in the heated reservoir chamber and perfused with blood by means of a Harvard peristalsic pump. The blood was maintained at 35° C throughout and was oxygenated by bubbling 95% oxygen and 5% carbon dioxide into the reservoir chamber. Flow rates were found to vary slightly from heart preparation to heart preparation and ranged from 150 to 250 ml/min. Perfusion pressure was maintained at 25 to 50 mm Hg and was used as a direct index of coronary vascular resistance. $R = (F/P)$ Flow = constant. A needle-tipped catheter connected to a Sanborn strain gauge and recorder was used to continously monitor the perfusion pressure. Needle-tipped electrodes were placed into the ventricles of the heart to monitor electrocardiogram and heart rate. Force of contraction was measured via a Walton-Brodie strain gauge arch sutured to the left ventricle.

Following a 30-minute equilibration period the blood flow to the heart was reduced by 50%. Five minutes after the reduction of coronary flow the change in force of contraction was measured. This reduction in force is expressed as percent change from control. In most preparations this procedure was repeated twice prior to the administration of β-hydroxy-γ-trimethylaminobutyric acid. The dose of β-hydroxy-γ-trimethylaminobutyric acid varied from 50 to 250 mg, and was injected directly into the inflow side of the perfusion circuit leading directly into the heart. At from 5 to 60 minutes after injection of β-hydroxy-γ-trimethylaminobutyric acid, the coronary blood flow was again reduced by 50% and the change in force measured. Only those hearts in which repeated measurement could be obtained were included in the study.

In each of the 20 isolated perfused hearts, a reduction in coronary flow produced a significant decrease in force of contraction. Percent decrease prior to administration of β-hydroxy-γ-trimethylaminobutyric acid varied from 55 to 85% with a mean of 71 ± 5. One hundred mg of β-hydroxy-γ-trimethylaminobutyric acid limited the percent decrease in force of contraction to from 19.6 ± 3.4 to 28.4 ± 7.9. At a dose of 150 mg, the present decrease in force was from 25.0 ± 7.2 to 29.5 ± 9.7. Following the administration of 200 mg, the decrease in force of contraction following a 50% reduction in blood flow was from 25.0 ± 6.4 to 27.3 ± 4.1. There is a significant difference between the control decrease in force of contraction and those noted following administration of β-hydroxy-γ-trimethylaminobutyric acid. In no instance was there an overlap between control and treated measurements of reduced flow ± standard deviation.

Restriction of blood flow to the dog myocardium by partial ligation of the anterior descending coronary artery is a useful model to study the effects of drugs in ischemic myocardial disease. In untreated (control) dogs, restricting coronary blood flow by 50% resulted in marked electrocardiographic changes including ST-segment elevation, which is a diagnostic feature of acute myocardial ischemia. Reducing coronary blood flow by 75% produced ventricular fibrillation.

Six dogs weighing about 10 – 12 kg were treated with DL-carnitine (100mg/kg, intravenously). Five minutes after drug administration the anterior descending coronary artery was occluded to reduce blood flow by 50%. In contrast to the six untreated animals, the dogs that were treated with carnitine had only minor alterations in electrocardiograms. Carnitine treatment resulted in a 90% reduction in ST-segment elevation compared to control dogs. When blood flow was reduced by 75%, carnitine treatment resulted in a 50 to 60% decrease in ST-segment elevation compared to control dogs. In addition, carnitine protected the hearts against ventricular fibrillation.

β-hydroxy-γ-trimethylaminobutyric acid also demonstrates a significant effect on failing heart-lung preparation, as can be seen from the following:

A series of 10 adult mongrel dogs were anesthetized with pentobarbital sodium, 30 mg/kg, and the chest of each opened via midline incision. The ascending aorta was cannulated by inserting a large bore polyethylene catheter into the brachiocephalic artery and advancing it into the aortic circulation. The descending aorta and the subclavian artery were then ligated following injection of heparin sodium, 1000 units/kg. The aortic catheter was connected to a heated blood bath into which all cardiac output was pumped. The bath was also connected to a second large catheter which was inserted into the superior vena cava. The azygos vein and the inferior cava were ligated. A bilateral vagotomy was performed. Aortic blood flow, heart rate, venous pressure, reservoir level and left ventricular force of contraction were continuously monitored. Resistance to aortic flow was then increased by 200% for 30 minutes, causing a progressive decrease in flow, heart rate and force of contraction. At 30 minutes, resistance to flow was decreased from 200% to 100% of control values. No significant recovery of force, rate or flow was noted in untreated heart-lung preparations. Those preparations given 250 mg/kg of β-hydroxy-γ-trimethylaminobutyric acid just prior to decreasing the resistance to flow at 30 minutes demonstrated a 50 to 75% of force of contraction, heart rate and flow rates. These changes persisted for 30 to 60 minutes or until termination of the experiment (usually at 1 to 1½ hours).

The effect of β-hydroxy-γ-trimethylaminobutyric acid on atrial flutter and ventricular arrhythmias associated with congestive heart failure, and a comparison with the corresponding effect of Quabain, can be seen from the following:

Twenty adult mongrel dogs, anesthetized with sodium pentobarbital, 30 mg/kg, were placed in severe heart failure using a method described by Gattschalk. Electrical stimuli were applied to the atrial appendages of the heart to induce atrial flutter and ventricular arrhythmias. Following 30 minutes of decreased cardiac work and ventricular arrhythmias, the dogs were given either Quabain (1 mg/kg) or β-hydroxy-γ-trimethylaminobutyric acid (20 mg/kg). Quabain produced a 40% ± 10% increase in the force of contraction, a 20% ± 5% decrease in the heart rate, and a 32% ± 5% increase in the cardiac output. Overall cardiac work increased 20% ± 2%. No anti-arrhythmiac effects were observed. The dogs treated with β-hydroxy-γ-trimethylaminobutyric acid showed an 85% ± 35% increase in force of contraction, a 40% ± 10% increase in heart rate, and a 90% ± 12% increase in cardiac output. Cardiac work increased 60% and 15%, and in 8 to 10 dogs, the arrhythmias were converted to a normal sinus rhythm.

The antiarrhythmic effect noted above can be more clearly seen in daunomycin-induced arrhythmias in both the Langendorff preparation and in intact Rhesus monkeys.

In a series of 20 isolated perfused Landendorff preparations, daunomycin was administered in a dose of 100 mg/kg thereby consistently producing ventricular arrhythmias, tachycardia, and severe arrhythmias. Following 30 minutes of the severe arrhythmias, β-hydroxy-γ-trimethylaminobutyric acid was administered in doses of from 50 mg to 500 mg. In 18 of the 20 isolated heart preparations, the arrhythmias noted were eliminated. The arrhythmias which were eliminated did not reappear for periods up to 60 to 90 minutes.

Twelve intact monkeys were likewise given daunomycin at a dose of 100 mg/kg. After 15 to 30 minutes of observed arrhythmias, β-hydroxy-γ-trimethylaminobutyric acid was administered intravenously in a dose of 100 to 250 mg. In 9 of the 12 intact monkeys preparations, the arrhythmias were eliminated. The monkeys were followed for from 8 to 12 hours using continuous recording techniques. No further arrhythmias were noted. No toxic manifestation was noted and all of the monkeys upon subsequent autopsy gave negative pathological reports.

The observations noted above in various laboratory models were confirmed in clinical studies which are briefly summarized below.

CASE 1

A patient wih carcinoma of the colon had both ureters implanted into his colon. Before surgery he was hypertensive and had a left branch block. After surgery, his blood pressure fell to 90/40. β-hydroxy-γ-trimethylaminobutyric acid was given as a single IV dose of 500 mg and within 60 seconds the blood pressure was 160/90. The cardiac rate fell from 105 to 85. The patient put out 615 cc of urine within an hour after β-hydroxy-γ-trimethylaminobutyric acid was given, 400 cc of which were excreted within the first 30 minutes. In the previous 9 hours there was a total urine output of less than 400 cc. His QRS complex on the EKG averaged 0.11 before administration and 2 minutes after administration averaged around 0.08–9. A few day later his blood pressure dropped from the previous consistent level of approximately 160/80 to 130/70. He was then given another dose of 500 mg IV and within 60 seconds his blood pressure rose to 180/80.

CASE 2

A similar type of operation, i.e., carcinoma of the colon and bilateral implantation of ureters, had been performed. The patient suddenly became hypotensive and entered the intensive care unit. He had a cardiac rate of 125 and the blood pressure was not detectable. A single IV dose of 500 mg of β-hydroxy-γ-trimethylaminobutyric acid was given. In 15 minutes, the systolic pressure was 80. Total urinary output for the 24 hours preceding this dose of β-hydroxy-γ-trimethylaminobutyric acid had 175 cc. The urinary output for 24 hours following β-hydroxy-γ-trimethylaminobutyric acid administration was 970 cc, a substantial portion of which occurred within an hour. The patient had atrial fibrillation before the administration of the drug which disappeared within 30 seconds. The normal sinus rhythm which occurred was maintained.

CASE 3

The patient, age 50, had a myocardia infarct with a history of hypertenstion. He went into cardiogenic shock and his blood pressure was not measureable. He responded to norepinephrine and his blood pressure rose to 85/65. He developed a gallop rhythm. He was given 500 mg of β-hydroxy-γ-trimethylaminobutyric acid in two doses thirty minutes apart. His blood pressure rose to 100/70 and his urinary output rose to 160 cc/hour (compared with a previous output of 10 cc/hour). The gallop rhythm remained.

CASE 4

A 63 year old male was hospitalized repeatedly for cardiac failure due to congestive heart failure. He had been treated for 14 years with cardiac glycosides and had intermittent cardiac irregularities. Upon this admission, the patient was found to be in cardiac failure with severe and continuing arrhythmias and no detectable blood pressure despite a continuous infusion of levophed. The patient was then given 500 mg of β-hydroxy-γ-trimethylaminobutyric acid. An immediate recovery of normal sinus rhythm, an improved cardiac output and a detectable blood pressure within the normal range were noted. Within 1 hour after administration, the patient, who had previously been anuric for 6½ hours, began to put out significant quantities of urine. This improved condition persisted for 24 hours. The patient received no further treatment with the drug.

CASE 5

A 42 year old male with a history of cardiovascular difficulties ranging from early hypertension to mitral valve replacement was admitted with congestive heart failure. The patient had previously been treated with coronary vasodilators and/or cardiac glycosides. Folowing 28 hours of supportive therapy, to which he was non-responsive, the patient was given 500 mg of β-hydroxy-γ-trimethylaminobutyric acid every 4 hours. The clinical response of the patient was evident within a few hours and he was essentially asymptomatic. After 7 days he was discharged from the hospital. β-hydroxy-γ-trimethylaminobutyric acid reversed both the cardiac arrhythmias and the congestive heart failure in this patient.

CASE 6

A 62 year old male suffered a myocardial infarct but demonstrated no acute cardiovascular difficulties. β-hydroxy-γ-trimethylaminobutyric acid was, nevertheless, given, in a dose of 500 mg, to determine whether there would be any cardiovascular effect. As expected, no detectable cardiovascular effect was observed over a period of 2 hours.

CASE 7

A 58 year old male was admitted with an acute myocardial infarct. He had no great difficulty with his blood pressure but had premature ventricular contractions as noted on the EKG. An intravenous dose of 500 mg of β-hydroxy-γ-trimethylaminobutyric acid was given and within a few minutes his PVC's were greatly diminished. A second dose was given 10 minutes after the first dose and within a few minutes the PVC's completely disappeared. There was no noticeable effect on blood pressure.

CASE 8

A 73 year old male patient with a large myocardial infarct entered the hospital in cardiogenic shock. Doses of 500 mg of β-hydroxy-γ-trimethylaminobutyric acid were given at 30-minute intervals. No detectable cardiovascular effect was observed.

CASE 9

A 65 year old male was admitted to the hospital with severe congestive heart failure with marked pulmonary and peripheral edema. He was given 500 mg of β-hydroxy-γ-trimethylaminobutyric acid every 15 minutes for over a period of approximately 1 hour, for a total of four doses. A diuresis immediately followed and within a period of 4 hours his clinical condition was markedly improved and his dyspnea virtually disappeared.

CASE 10

A 78 year old female was scheduled for a cholecystectomy. Her pulse was 55 (left bundle branch block) and the anesthesiologist would not handle the patient until her pulse was higher. Atropine was given without a response. An automatic cardiac pacemaker was inserted and the patient's pulse rate went to 80. After surgery the patient did well until the pacemaker was turned off. Her pulse immediately fell to 58–60. β-hydroxy-γ-trimethylaminobutyric acid was administered and her pulse immediately went to 76. This same phenomena occurred twice with the next hour; i.e., pulse fell and the drug reversed the fall. After the second administration, the patient was once again placed on the pacemaker. When the pacemaker was turned off the pulse immediately fell. The third dose of β-hydroxy-γ-trimethylaminobutyric acid was then given and the pulse immediately rose. From that point on the pacemaker was not required to maintain a regular pulse that was 70 or over.

CASE 11

A 63 year old female was operated upon to correct a small bowel fistula. She had cancer of the bladder and had undergone bladder irradiation. Postoperatively she had escessive vaginal bleeding that was emanating from the bladder. Her blood pressure began to fall and her pulse rate increased. Eventually, her blood pressure was undetectable and her pulse fell to 60. β-hydroxy-γ-trimethylaminobutyric acid, 500 mg. was given and almost immediately her systolic pressure rose to 90 and her pulse to 100–120. In approximately 1 hour, her blood pressure was again undetectable and her pulse rate was 50. Once more 500 mg of β-hydroxy-γ-trimethylaminobutyric acid was given and during β-hydroxy-γ-trimethylaminobutyric acid administration her systolic blood pressure rose to 90 and her pulse to 100. Additional administration of the drug was not made.

CASE 12

An 86 year old male was admitted with a diagnosis of severe anemia and congestive heart failure. He was found to have carcinoma of the colon. He was digitalized and given 5 pints of blood whereupon he was operated upon. Following surgery his EKG showed many ectopic beats and a bundle branch block. Extrasystoles became quite prominent. Blood pressure was 134/80 and pulse 58. He was given 500 mg of β-hydroxy-γ-trimethylaminobutyric acid intravenously over a 5 minute period and before drug administration was completed, the cardiac arrhythmias were markedly reduced. He had previously failed to respond to atropine. Three subsequent doses were given over a period of an hour whereupon his arrhythmia disappeared except for an occasional ectopic beat. His P-R interval shortened to a first degree heart block. A normal sinus rhythm continued throughout his hospital stay. Digitalis was stopped before surgery.

Arrhythmias induced by the experimental removal of a heart from an anesthesized intact dog preparatory to the Langendorff perfusion technique occur in approximately 50 percent of the hearts isolated. These arrhythmias are varied and are both atrial (in 20 cases) and venticular (in 16 cases) in nature. In 20 arrhythmic isolated dog hearts carnitine (100 mg, parenteral single dose) eliminated all arrhythmias and restored normal sinus rhythm.

As part of the open-chest experimental procedure hearts of anesthesized dogs were exposed via a midline chest incision. The atrium of the heart was electrically stimulated to cause atrial flutter and fibrillation subsequent ventricular arrhythmias in 20 such preparations, Carnitine when administered intravenously in doses of 50–250 mg, eliminated the atrial and ventricular arrhythmias occurring in all preparations.

12 cats were similarly treated by electrical stimulations of the atrium of the heart to cause atrial flutter and fibrillation. Administration of 20 mg/kg of carnitine i.v. produced a slight anti-arrhythmic effect. Administration of 50 mg/kg of carnitine i.v. returned the rhythms to normal. Administration of 100 mg/kg of carnitine i.v. also returned the rhythms to normal and resulted in a longer lasting effect than 50 mg/kg.

Twenty isolated dogs hearts treated with 100 mg/kg of daunomycin resulted in severe atrial and ventricular arrhythmias in all preparations. When carnitine was administered in a single dose of 100–250 mg parenteral, the arrhythmias were eliminated in 18 of 20 preparations.

Intact monkeys: daunomycin (100 mg/kg) caused severe atrial and ventricular arrhythmias in 12 intact monkeys. In 9 of the 12 animals the severe arrhythmias were completely eliminated by carnitine (single dose of 100–250 mg i.v.).

Isolated dog hearts: Adriamycin, an analogue of daunomycin, exerts an arrhythmic effect similar to that induced by daunomycin. In six langendorff heart preparations, all hearts were protected from the arrhythmic effect of 100 mg/kg adriamycin by carnitine administration (100–250 mg parenteral).

β-hydroxy-γ-trimethylaminobutyric acid contains a center of asymmetry and thus exists in two sterioisomers. Either the racemate or the individual isomers can be employed. While the racemate can be conveniently employed, it appears the L-isomer is more active while the D-isomer is slightly more toxic. Thus the $LD_{50}$ in the mouse is as follows:

|  | Subcutaneous | Intraperitoneal |
|---|---|---|
| Racemate | 11.5 g/kg | 12 g/kg |
| L-isomer | 13.8 | 14 |
| D-isomer | 10.5 | 10 |

The test data set forth above is illustrative of the use of carnitine and its pharmaceutically acceptable non-toxic salts for improving the myocardial function of a human or animal heart to which the oxygen supply has been diminished by parenterally administering to a human or animal whose heart's oxygen supply has been diminished an amount of active agent sufficient to improve the myocardial function. The preferred method of parenteral administration is intravenous. Preferably either carnitine or the hydrochloride salt thereof is administered.

Fluid unit dosage forms for parenteral administration are prepared by suspending or dissolving a measured amount of β-hydroxy-γ-trimethylaminobutyric acid in a non-toxic liquid vehicle suitable for injection, such as an aqueous or oleagenous medium, and sterilizing the suspension or solution. Alternatively a measured amount of β-hydroxy-γ-trimethylaminobutyric acid is placed in a vial and the vial and it contents are sterilized and sealed. An accompanying vial or vehicle can be provided for mixing prior to administration.

Of the above fluid unit dosage forms intended for injection, in particular intravenous and intramuscular injection, are preferred. The sterile liquid or fluid injectible unit dosage forms are the compositions of choice.

In addition to the free base, which can exist in Zwitterionic form, one can employ pharmaceutically acceptable salts such as the hydrochloride (m.p. 142°). Since however β-hydroxy-γ-trimethylaminobutyric acid as the free base is itself soluble in aqueous media, utilization of a salt for solubility purposes is generally not necessary.

The dose which is administered must of course be determined from the age, weight and condition of the patient, utilizing sound professional judgement. An effect can be observed at doses as low as 1 to 2 mg/kg but generally the dose is from about 5 to about 10 mg/kg. Larger doses can be given with relative safety in view of the low toxicity of the compound and such doses are often indicated when an insufficient response indicates an insufficient initial dose for the particular patient. Utilization of oral unit dosage forms also requires a somewhat larger dose than is employed in the case of parenteral administration.

EXAMPLE

A sterile aqueous suspension for intramuscular injection, containing in each ml. 100 mg of β-hydroxy-γ-trimethylaminobutyric acid, is prepared from the following ingredients:

| | | |
|---|---|---|
| β-hydroxy-γ-trimethylaminobutyric acid | gm | 100 |
| Sodium carboxymethylcellulose, low viscosity | gm | 10 |
| Polysorbate 80, U.S.P. | gm | 4 |
| Propylparaben, U.S.P. | gm | 0.4 |
| Water for injection q.s. | gm | 1,000 |

What is claimed is:

1. A method of improving the myocardial function of a human or animal heart when the oxygen supply to said heart has been diminished which comprises administering to a human or animal whose heart's oxygen supply has been diminished, an amount of β-hydroxy-γ-trimethylaminobutyric acid or a pharmaceutically acceptable non-toxic salt thereof, sufficient to improve the myocardial function.

2. A method according to claim 1 wherein the administration is intravenous

3. A method according to claim 1 wherein β-hydroxy-γ-trimethylaminobutyric acid is administered.

4. A method according to claim 1 wherein the hydrochloride salt of β-hydroxy-γ-trimethylaminobutyric acid is administered.

5. A method according to claim 1 wherein the administration is parenteral.